United States Patent [19]

Callaway

[11] Patent Number: 4,993,411
[45] Date of Patent: Feb. 19, 1991

[54] ULTRASONIC OXYGEN HUMIDIFIER

[75] Inventor: James J. Callaway, Franklin, Tenn.

[73] Assignee: Medway, Franklin, Tenn.

[21] Appl. No.: 505,510

[22] Filed: Apr. 6, 1990

[51] Int. Cl.$^5$ .............................................. A61M 11/00
[52] U.S. Cl. .......................... 128/204.14; 128/200.16;
128/200.14; 128/203.12; 261/DIG. 65
[58] Field of Search ...................... 128/200.16, 204.14,
128/200.14, 203.12; 261/DIG. 65

[56] References Cited

U.S. PATENT DOCUMENTS

| | | | |
|---|---|---|---|
| 2,852,022 | 9/1958 | Netteland | 128/200.17 |
| 3,387,607 | 6/1968 | Gauthier et al. | 128/200.16 |
| 3,593,712 | 7/1971 | Weaver | 128/200.16 |
| 3,901,443 | 8/1975 | Mitsui et al. | 239/102.2 |
| 4,243,396 | 1/1981 | Cronenberg | 55/238 |
| 4,319,155 | 3/1982 | Nakai et al. | 310/316 |
| 4,463,708 | 8/1984 | Gerry | 123/25 E |
| 4,776,990 | 10/1988 | Verity | 261/128 |

OTHER PUBLICATIONS

New Riverside University Dictionary; 1984 Ed., Houghton Mifflin, Co.

Primary Examiner—Edgar S. Burr
Assistant Examiner—Eric P. Raciti
Attorney, Agent, or Firm—Fleit, Jacobson, Cohn, Price, Holman & Stern

[57] ABSTRACT

A closed vertical mixing chamber is defined above a predetermined plan area of a body of water and an upright tubular member including open upper and lower ends is supported over a central zone of the area spaced slightly above the water level. Structure is provided defining a closed inlet chamber above lower end of the tubular member and about the latter into which gas to be humidified is admitted. The gas is discharged downwardly from the inlet chamber about the lower end of the tubular member toward the water level and at locations spaced outwardly from and about the tubular and electro-acoustical transducer structure is operatively associated with the water in the zone for generating a column of water projecting upwardly above the level and having finely divided particles of water emanating therefrom. The gas moves inwardly over the surface of the water toward the water column and thereafter upwardly into the tubular member about the water column. The upper end of the tubular member opens into the upper end portion of the mixing chamber for discharging humidified gas thereinto and a gas outlet is provided opening outwardly of a lower portion of the mixing chamber adjacent the lower end of the tubular member.

13 Claims, 2 Drawing Sheets

ULTRASONIC OXYGEN HUMIDIFIER

BACKGROUND OF THE INVENTION

1. Field of the Invention

An apparatus is provided for generating, upon a predetermined surface area of a body of water, an upwardly projecting ultrasonically activated column of water having finely divided water particles thereabout and thereabove and the lower end of a vertical tube or chimney is spaced slightly above the water level and about the water column. Dry oxygen under pressure is introduced into a closed inlet chamber disposed about the lower end of the chimney. The oxygen is passed over the surface of the water toward and upwardly about the water column and into the chimney for humidification by the ultrasonically divided water particles. The humidified oxygen and remaining non-evaporated particles of water then pass upwardly through the chimney and laterally outwardly into a closed mixing chamber disposed about the upper end of the chimney. The oxygen and remaining finely divided particles of water then pass downwardly through the mixing chamber in a swirling motion to ensure substantial evaporation of the remaining fine water particles before discharge of the humidified oxygen laterally outward from the bottom of the mixing chamber.

2. Description of Related Art

Various different forms of gas humidifying devices including some of the general structural and operational features of the instant invention heretofore have been provided. Examples of these previously known devices are disclosed in U.S. Pat. Nos. 2,852,022, 3,387,607, 3,593,712, 4,243,396, 4,319,155 and 4,776,990. However, these previously known devices do not include the overall combination of structural features of the instant invention nor do they disclose the specific path of gas to be humidified both immediately prior and subsequent to the co-mingling of water vapor and finely divided water particles during the water evaporation process before discharge of humidified oxygen from the humidifier. The prior devices do not feature application of ultrasonically generated water vapor to oxygen used in medical therapy.

SUMMARY OF THE INVENTION

The invention herein described is intended for administering oxygen for treatment of medical patients. It addresses and solves the problems which in the past have been accepted as the "price one pays" for the life saving result of oxygen therapy.

Oxygen, as provided to hospitals (or homes), is delivered to the user as a compressed gas and is stored in high pressure cylinders for home use or in central tanks from which it is distributed through a network of pipes, valves and regulators to individual patients in a hospital or the like.

Separation of oxygen from air involves the process of compressing air to the point of liquefaction and, thereafter, oxygen can then be liberated from nitrogen and other less important gasses by fractional distillation. This process also separates any moisture which may have been in the original volume of air before the compression process. Therefore, when the compressed oxygen is expanded to normal atmospheric pressure it is extremely dry. If administered to a patient in this condition over a long period, the dry oxygen will dehydrate the nasal passages and the respiratory tract, causing discomfort and possible damage to the patient's air passages.

To avoid this problem, it is necessary to add moisture to the oxygen before it is administered to the patient. In existing humidification systems, this is done by (1) bubbling the oxygen through a closed container of water or by (2) atomizing the water from a container, whereby the flow of oxygen over an orifice provides the energy for breaking up the water into fine particles for easy vaporization in the stream of gas.

Both of the above systems are not as efficient as desired, in that there is little or no control over the amount of moisture introduced into the gas stream. Changes in the gas flow rate change the humidity of the mixture available for breathing. To assure ample moisture, the system necessarily is set to bring the moisture level to saturation. This causes secondary problems such as condensation in the supply tubes and masks resulting in spillage of water on the patient or his (or her) bedding. The second system presents a unique problem, in that the use of oxygen as the working fluid for atomization requires an excessive rate of oxygen flow and is therefore, relatively expensive to operate.

The humidifier of the instant invention provides a means of controlling the introduction of water vapor into the oxygen flow such that patient comfort and medical needs are met while reducing the inconvenience of excessive water and high oxygen usage.

The main object of this invention is to provide a humidifier for dry medicinal oxygen which will be capable of humidifying medicinal oxygen to a level of between 60% to 90% humidity.

Another object of this invention is to provide a humidifier in accordance with the preceding object which may be adjusted to vary the humidity of the humidified oxygen, as desired.

Still another object of this invention is to provide a humidifier which will be adjustable as to the humidity of oxygen discharged therefrom independent of the flow rate of oxygen therethrough.

A still further object of this invention is to provide an oxygen humidifier operative to humidify medicinal oxygen to between 60% and 90% relative humidity while using only so much oxygen as is required by an attendant patient.

Another very important object of this invention is to provide an oxygen humidifier offering a visual indication of the gas flow through the humidifier approximately mid-length the flow passage for humidified oxygen passing through the humidifier.

A final object of this invention to be specifically enumerated herein is to provide an ultrasonic humidifier in accordance with the preceding objects and which will conform to conventional forms of manufacture, be of simple construction and easy to use so as to provide a device that will be economically feasible, long-lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
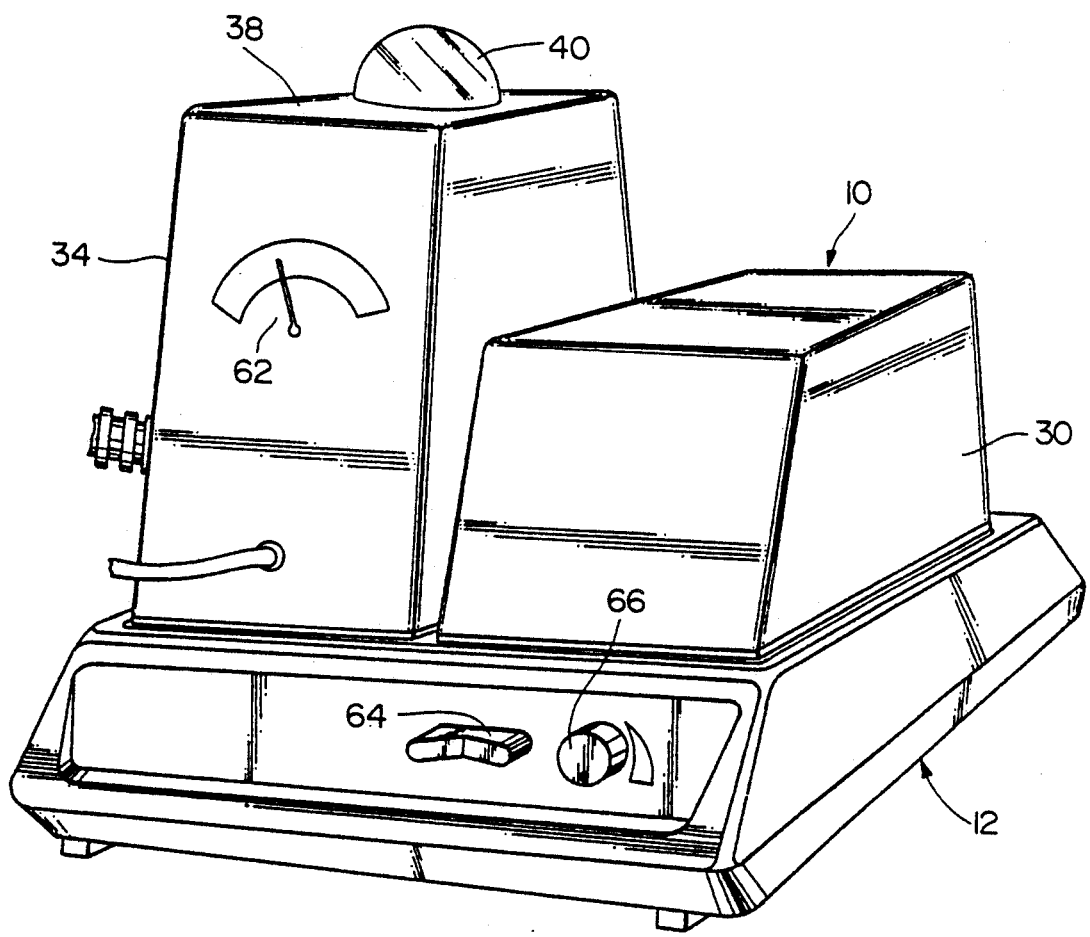
FIG. 1 is a front perspective view of the ultrasonic humidifier of the instant invention.

Referring now more specifically to the drawings the numeral 10 generally designates the ultrasonic humidifier of the instant invention. The humidifier 10 includes a base generally referred to by the reference numeral 12 and the base 12 defines an upwardly opening water reservoir 14 beneath which an electro-acoustical transducer 16 is mounted, the transducer 16 being in direct communication with the water 18 in the reservoir 14 through an opening 20 formed in a downwardly offset portion 22 of the bottom wall 24 for the reservoir 14. A variable control 26 is mounted beneath the bottom wall and electrically connected to the transducer 16 in any convenient manner for adjustably varying the amplitude of the transducer 16 output, the control 26 including electrical conductor means for supplying the control 26 with electrical energy from any suitable source (not shown) of electrical potential.

An inverted water container 30 is supported from the right hand side of the base 12 with the outlet neck of the container 30 projecting down into the reservoir 14 to the desired water level 32.

The left hand side of the base 12 has an inverted downwardly opening closure or hollow housing 34 supported therefrom with the downwardly opening lower end 36 of the housing 34 projecting down into the reservoir 14 to a level spaced below the water level 32. The upper end of the closure or hollow housing 34 is closed by a top wall 38 including a central upwardly projecting hemispherical protrusion or projection 40 which is transparent and an upright tube 42 is centrally disposed within the housing 34 and has its lower end spaced slightly above the water level 32 in substantially vertical registry with the opening 20. The upper and lower ends of the tube 42 are open, but one side portion of the upper end of the tube 42 includes a partial cylindrical inwardly projecting wall portion 44 for a purpose to be hereinafter more fully set forth.

The tube 42 includes annular partition 46 supported therefrom adjacent its lower end and the partition 46 divides the interior of the housing 34 into upper and lower chamber sections 48 and 50, the housing 34 including a humidified oxygen outlet 52 closely above the partition 46 and a dry oxygen inlet 54 immediately below the partition 46. Also, a foraminated partition 56 is disposed in the lower chamber section 50 below the oxygen inlet 54 and above the lower end of the tube 42. The partition 56 defines a gas distribution partition.

Figure 2:
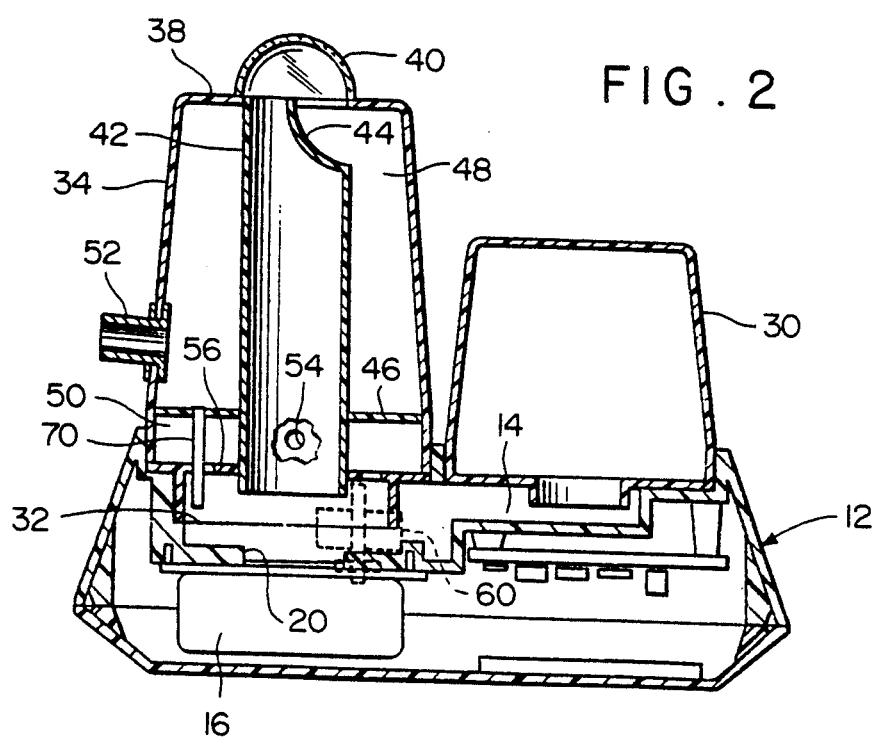
FIG. 2 is a reduced scale transverse vertical sectional view of the humidifier.
Figure 3:
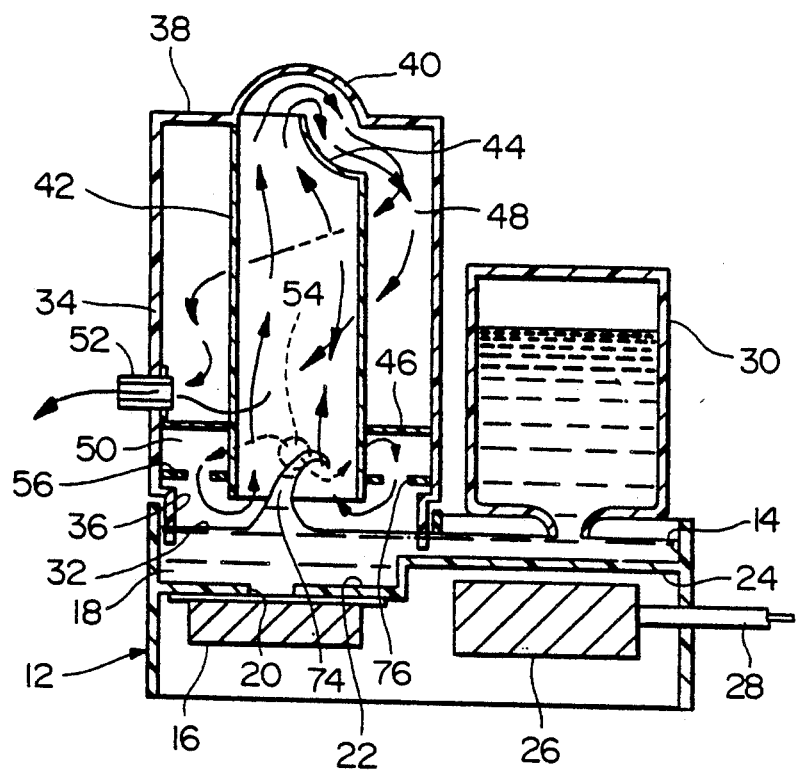
FIG. 3 is a schematic transverse vertical sectional view of the humidifier illustrating the water supply, water level and the oxygen and water vapor passages through the humidifier.
Figure 4:
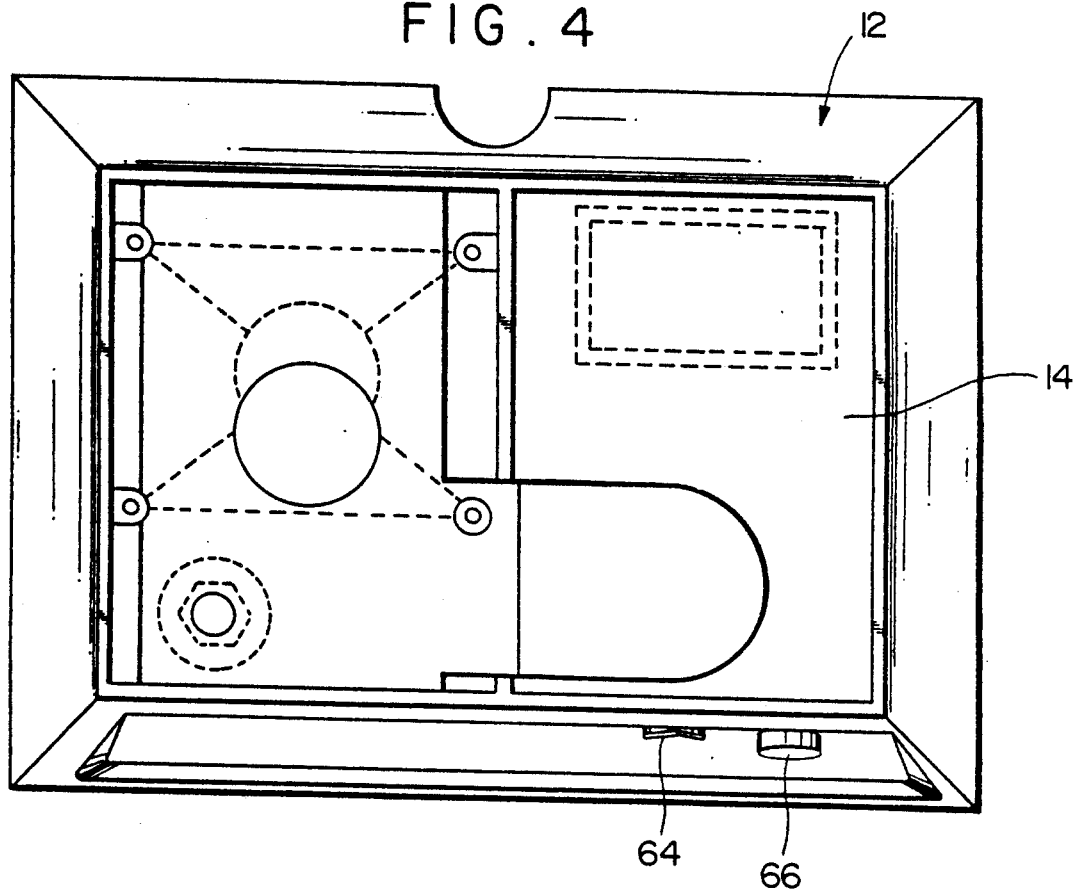
FIG. 4 is an enlarged top plan view of the base of the humidifier.

If is desired, the inverted water container 30 could be omitted and the corresponding side of the top portion of the base 12 could be closed and water within the reservoir 14 could be maintained at the level 32 from a suitable source of water under pressure under the control of a float operated valve such as that indicated at 60 in FIG. 2, it being only necessary that the water level 32 be maintained substantially as that illustrated in FIG. 3.

The cover or hollow housing 34 may be provided with a humidity indicating gauge 62 readable from the exterior of the housing 34 and operative to indicate the humidity of oxygen passing downwardly through the upper chamber section 48. In addition, the control 26 may be provided with an on-off control 64 on the front wall of the base 12 as well as a variable control 66 operatively associated with the control 26 for varying the amplitude developed by the transducer 16.

Still further, a drain tube 70, see FIG. 2, opens upwardly through the partition 46 to drain any moisture which may collect on the bottom of the upper chamber section 48 down into the water 18 within the reservoir 14.

In operation, when the humidifier 10 is provided with water in the manner illustrated in FIG. 3, dry oxygen is admitted into the lower chamber section 50 above the partition 56 and below the partition 46 as at 54. The dry oxygen is admitted into the lower chamber section 50 only at the rate oxygen is to be delivered to the patient. The control 64 is actuated to effect operation of the transducer and the control 66 is initially adjusted to a predetermined position. Operation of the transducer 16 causes a column 74 of water to project above the level 32 and into the lower end of the tube 42 in the manner illustrated in FIG. 3. In addition to the column 74, the column 74 is surrounded, all side and above, by finely divided water particles and the foraminated partition 56 breaks up the initial inlet stream of dry oxygen into a plurality of individual streams of oxygen passing downwardly through the circumferentially spaced openings 76 formed in the partition 56. These individual streams of dry oxygen flow downwardly toward the water level 32, inwardly along the latter to the column 74 and then up into the lower end of the tube 42 on all sides of the column 74. As the individual streams of oxygen entering the lower chamber section 50 below the partition 56 move inwardly toward the column 74 and up into the lower end of the tube 42 they pass along side the column 74 and pick up some of the finely divided water particles thereabout and thereabove. Inasmuch as the oxygen entering the humidifier 10 is initially extremely dry, most of the finely divided water particles picked up in the movement of gas upwardly through the tube 42 are immediately evaporated, although some finely divided water particles may remain.

As the flow of humidified gas is discharged from the upper end of the tube 42 into the right hand portion of the projection 40 as seen in FIG. 3, the amount of non-vaporized moisture in the gas flow may be visually observed through the transparent projection 40. Thereafter, the humidified gas flows downwardly along side the right hand portion of the tube 42 defined by the wall portion 44 and thereafter into the upper chamber section 48 for movement about all sides of the tube 42 while moving downwardly through the upper chamber section 48 for subsequent discharge through the outlet 52 leading toward a patient. As the gas flow moves downwardly through the upper chamber section 48 and about the tube 42, substantially all of the remaining finely divided water particles are finally evaporated. Of course, the control 66 is adjusted so that only minimum water vapor may be observed through the transparent projection 40, thereby insuring substantially full evaporation of all water particles by the time the humidified oxygen is discharged from the humidifier 10 through the outlet 52.

If the rate of flow of oxygen into the humidifier 10 as at 54 is increased, the power output to the transducer 16 through the control 26 is proportionately increased to maintain the same relative humidity of oxygen discharged from the outlet 52.

By confining the oxygen flow to an upward path along all sides and above the column 74 and for a considerable height thereabove, substantially all finely divided water particles may be evaporated by the time the gas flow passes beneath the transparent projection 40.

Thus, in addition to the gauge 62, a visual indication of the evaporation process of the finely divided water particles in the oxygen flowing upwardly through the tube 42 and being discharged therefrom may be gained through the projection 40 prior to the humidified oxygen completing its path of movement through the humidifier 10. Also, the gas flow is slightly compressed in the area of the discharge of oxygen from the upper end of the tube 42 in view of the reduced cross sectional area of the gas flow outlet defined by the upper end of the tube 42 and the projection 40 and after the gas flow passes from beneath the projection 40 it is laterally discharged by wall portion 44 in a swirling manner and expanded to a slight degree upon movement into the upper chamber section 48, thereby further enhancing the ability of the oxygen to evaporate any remaining finely divided water particles before the oxygen is discharged from the vaporizer 10 through the outlet 52. Still further, after the gas flow is slightly expanded upon entering the upper chamber section 48 disposed about the upper end of the tube 42, the continued swirling movement of the gas flow downwardly about the tube 42 toward the outlet 52 further enhances evaporation of any remaining finely divided particles of water.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A gas humidifying apparatus defining a reservoir containing a liquid therein to a predetermined level, closure means defining a closed vertical chamber above said level, closed at its lower end by said liquid, an electro-acoustical transducer operatively associated with said reservoir below said level and in conjunction with said liquid in said reservoir to said level and by vibration of said liquid at ultrasonic frequency and with sufficient amplitude to develop a localized column of said liquid above said level as well as finely divided water particles emanating from said column, an upright tube within said chamber including open upper and lower ends, said lower end being vertically registered with said column, spaced outwardly therefrom and closely spaced above said level, partition means in said chamber adjacent and spaced above said level and about the lower end portion of said tube and dividing said chamber, outwardly of said tube, into upper and lower chamber sections into which the upper and lower ends, respectively, of said tube open, gas inlet means opening into said lower chamber section for discharging gas under controlled pressure into said lower chamber section, and humidified gas outlet means opening outwardly of said upper chamber section, a foraminated gas distribution partition in said chamber spaced below said partition means above said level and about the lower end portion of said tube defining a gas inlet chamber below and above said upper and lower chamber sections into which said gas inlet means opens.

2. The apparatus of claim 1 wherein said humidified gas outlet opens outwardly of the lower half of said upper chamber section and said upper end of said tube opens outwardly into the upper half of said upper chamber section.

3. The apparatus of claim 1 wherein said liquid comprises water and said gas inlet means comprises inlet means for oxygen.

4. The assembly of claim 1 wherein said electro-acoustical transducer includes a variable control therefore for varying the amplitude of the output thereof.

5. A gas humidifying apparatus defining a reservoir containing liquid therein to a predetermined level, closure means defining a closed vertical chamber above said level, closed at its lower end by said liquid, an electro-acoustical transducer operatively associated with said reservoir below said level and in conjunction with said liquid in said reservoir to said level and by vibration of said liquid at ultrasonic frequency and with sufficient amplitude to develop a localized column of said liquid above said level as well as finely divided water particles emanating from said column, an upright tube within said chamber including open upper and lower ends, said lower end being vertically registered with said column, spaced outwardly therefrom and closely spaced above said level, partition means in said chamber adjacent and spaced above said level and about the lower end portion of said tube and dividing said chamber, outwardly of said tube, into upper and lower chamber sections into which the upper and lower ends, respectively, of said tube open, gas inlet means opening into said lower chamber section for discharging gas under controlled pressure into said lower chamber section, and humidified gas outlet means opening outwardly of said upper chamber section, said closure means incorporating a top wall including a transparent bulbous portion thereof spaced closely above the upper end of said tube for viewing the amount of vapor being discharged from said tube upper end from the exterior of said closure means.

6. The apparatus of claim 5 wherein the open upper end of said tube opening into said transparent bulbous portion comprises a reduced cross sectional area outlet for the upper end of said tube.

7. The apparatus of claim 6 wherein said electro-acoustical transducer includes a variable control therefore for varying the amplitude of the output thereof.

8. The apparatus of claim 7 including a foraminated gas distribution partition in said chamber spaced below said partition means above said level and about the lower end portion of said tube defining a gas inlet chamber below and above said upper and lower chamber sections into which said gas inlet means opens.

9. The apparatus of claim 8 wherein said liquid comprises water and said gas inlet means comprises inlet means for oxygen.

10. In a humidifier including a reservoir containing water to a predetermined level, means defining a closed mixing chamber above said level, an upright tubular member having open upper and lower ends supported within said mixing chamber with said lower end spaced slightly above said level, chamber defining means defining a closed gas inlet chamber above said lower end and about the latter into which gas to be humidified is admitted into said closed inlet chamber, said chamber defining means including gas discharge means operative to downwardly discharge gas from said inlet chamber about said lower end of said tubular member toward said level and at a plurality of locations spaced evenly about and outwardly from said lower end, electro-acoustical transducer means operatively associated with said reservoir and the water therein in said zone for generating a column of water projecting upwardly above said level, in said zone and having finely divided particles of water emanating therefrom, said upper end opening outwardly into an upper portion of said mixing chamber, and humidified gas outlet means opening outwardly of a lower portion of said inlet chamber.

11. The humidifier of claim 10 wherein said mixing chamber is closed at its upper end by a transparent wall portion upwardly toward which said upper end of said tubular member opens.

12. The humidifier of claim 11 wherein said open upper end of said tubular member is reduced in cross sectional area relative to the cross sectional area of the lower end of said tubular member.

13. The method of obtaining at least substantial full evaporation of water by oxygen during an oxygen humidification process wherein medicinal dry oxygen is being humidified to between 60% and 90% relative humidity, said method including, in combination with a body of water and a closed chamber sealed relative to and disposed over the surface of said body of water and including a transparent upper wall portion forming at least a portion of an upper end closure for said chamber, providing an upstanding chimney within said chamber having an open lower end spaced slightly above a predetermined area of the surface of said body of water and an open upper end spaced slightly below said transparent wall portion, providing a partition in said chamber above said lower end to divide said chamber into closed upper and lower chamber sections, acting upon said body of water by a variable amplitude electro-acoustical transducer to generate a column of water projecting upwardly from a central zone of said predetermined area of said surface as well as finely divided water particles emanating from said column, causing dry oxygen to pass over said surface toward said column from all sides thereof, upwardly into and through said chimney and outwardly of the latter and into an upper portion of said upper chamber section and thereafter downwardly through said upper chamber section about said chimney and outwardly from a lower portion of said upper chamber section for conveyance to a patient, and varying the amplitude of said transducer such that only a slight amount of water vapor may be observed through said transparent wall portion in the oxygen being discharged from the upper end of said chimney into said upper chamber section.

* * * * *